United States Patent
Christians

(10) Patent No.: US 9,719,081 B2
(45) Date of Patent: *Aug. 1, 2017

(54) THERMOSTABLE BLUNT-END LIGASE AND METHODS OF USE

(71) Applicant: Theranos, Inc., Palo Alto, CA (US)

(72) Inventor: Frederick Christians, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,013

(22) Filed: Jan. 20, 2016

(65) Prior Publication Data

US 2017/0015989 A1 Jan. 19, 2017

Related U.S. Application Data

(63) Continuation of application No. 14/214,834, filed on Mar. 15, 2014, now Pat. No. 9,273,301.

(60) Provisional application No. 61/802,124, filed on Mar. 15, 2013.

(51) Int. Cl.
| C12N 9/00 | (2006.01) |
| C12P 19/34 | (2006.01) |

(52) U.S. Cl.
CPC ............... *C12N 9/93* (2013.01); *C12P 19/34* (2013.01); *C12Y 605/01001* (2013.01); *C07K 2319/21* (2013.01); *C07K 2319/80* (2013.01)

(58) Field of Classification Search
None
See application file for complete search history.

(56) References Cited

U.S. PATENT DOCUMENTS

| 7,208,278 B2 | 4/2007 | Chen et al. |
| 7,927,853 B2 | 4/2011 | Nishida et al. |
| 9,273,301 B2 * | 3/2016 | Christians ............... C12N 9/93 |
| 2012/0214208 A1 | 8/2012 | Patrick et al. |
| 2014/0273102 A1 | 9/2014 | Christians |

FOREIGN PATENT DOCUMENTS

| WO | 9402615 A1 | 2/1994 |
| WO | 2011034449 A1 | 3/2011 |
| WO | 2015076919 A1 | 5/2015 |

OTHER PUBLICATIONS

Chica el al. Semi-rational approaches to engineering enzyme activity: combining the benefits of directed evolution and rational design. Curr Opin Biotechnol. Aug. 2005; 16(4):378-84.
Database UniPortKB/TrEMBL, I3RFS7 (I3RFS7_9EURY), Sep. 5, 2012.
De Lumley et al. A biophysical characterisation of factors controlling dimerisation and selectivity in the NF-kappaB and NFAT families. J. Mol. Biol. 339:1059-1075 (2004).
International Search Report and Written Opinion dated Aug. 7, 2014 for Application No. PCT/US2014/030003.
Lauer Gail et al. Cloning, Nucleotide Sequence, and Engineered Expression of Thermus thermophilus DNA Ligase, a Homolog of *Escherichia coli* DNA Ligase. Journal of Bacteriology, Aug. 1991, vol. 173, No. 16, pp. 5047-5053.
Notice of Allowance dated Oct. 28, 2015 for U.S. Appl. No. 14/214,834.
Office Action dated Jul. 21, 2015 for U.S. Appl. No. 14/214,834.
Preliminary Amendment dated Sep. 4, 2015 for U.S. Appl. No. 14/846,285.
Rolland et al. Characterization of a thermophilic DNA ligase from the archaeon Thermococcus fumicolans. FEMS Microbiol. Lett. 236:267-273 (2004).
Sen et el. Developments in Directed Evolution for Improving Enzyme Functions. Appl Biochem Biotechnol. Dec. 2007;143(3)212-23.
Wilson et al. Engineered DNA ligases with improved activities in vitro Protein Engineering Design & Selection 26 (7)471-478 (2013).

* cited by examiner

*Primary Examiner* — Christian Fronda

(57) ABSTRACT

Fusion proteins having thermostable blunt-end ligase activity are provided. Blunt-end ligases are useful for DNA amplification, sequencing, production of recombinant DNA and recombinant fusion proteins, and other purposes. These thermostable blunt-end DNA ligases are useful in ligation schemes which include, e.g., an incubation at about 60-65° C. or higher, or as high as about 94° C., or at other temperatures. The ligases disclosed herein may enable high temperature blunt-end ligation without need for molecular crowding agents, and so may be useful for many nucleic acid ligation-amplification schemes, e.g., ones which operate at a uniform temperature (e.g., at about 60° C. or higher), including ones which require temperature cycling, e.g., from about 94° C. to about 60° C. (or higher) for one, two, three, or more cycles. The thermostable blunt-end DNA ligases disclosed herein enable higher specificity target amplification, for example, by permitting temperature denaturation of double-stranded DNA templates as well as specific primer binding.

20 Claims, 1 Drawing Sheet

APPENDIX A

| EE0139 | /5Phos/AATTCTCTTTAAATAAACCCAAGGTCTCAGATTTCATGCAGATTGTGTC<br>SEQ ID NO: 9 |
|---|---|
| EE0140 | /5Phos/GACACAATCTGCATGAAATCTGAGACCTTGGGTTTATTTAAAGAGAATT<br>SEQ ID NO: 10 |

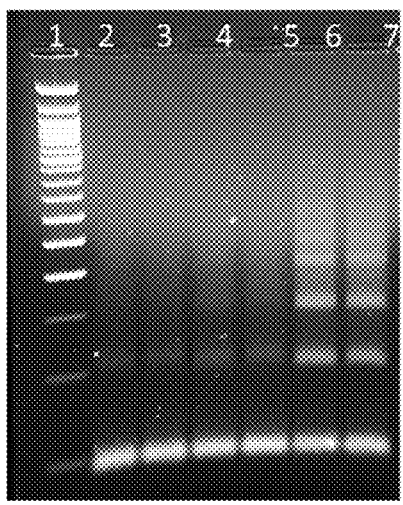

| Well | Ligase | Template | Ligase Conc | Temp |
|---|---|---|---|---|
| 1 | Standard 50bp | | | |
| 2 | RDP71 | Tth Ligase | EE139/EE140 | 1uM | 75C |
| 3 | RDP71 | Tth Ligase | EE139/EE140 | 1uM | 75C |
| 4 | RDP75 | T4 Ligase P50 | EE139/EE140 | 1uM | 75C |
| 5 | RDP75 | T4 Ligase P50 | EE139/EE140 | 1uM | 75C |
| 6 | RDP78 | Tth-p50 | EE139/EE140 | 1uM | 75C |
| 7 | RDP78 | Tth-p50 | EE139/EE140 | 1uM | 75C |

Ligation reaction = 30mins @ 75C

← 49-bp template

SEQUENCE LISTING

<160> NUMBER OF SEQ ID NOS: 11

<210> SEQ ID NO 1
<211> LENGTH: 10
<212> TYPE: DNA
<213> ORGANISM: Unknown
<220> FEATURE:
<223> OTHER INFORMATION: Description of Unknown: Unknown natural target
      p50 sequence

<400> SEQUENCE: 1
gggaattccc                                                                 10

<210> SEQ ID NO 2
<211> LENGTH: 327
<212> TYPE: PRT
<213> ORGANISM: Homo sapiens

<400> SEQUENCE: 2

Ala Asp Gly Pro Tyr Leu Gln Ile Leu Glu Gln Pro Lys Gln Arg Gly
1               5                   10                  15

Phe Arg Phe Arg Tyr Val Cys Glu Gly Pro Ser His Gly Gly Leu Pro
                20                  25                  30

Gly Ala Ser Ser Glu Lys Asn Lys Lys Ser Tyr Pro Gln Val Lys Ile
            35                  40                  45

Cys Asn Tyr Val Gly Pro Ala Lys Val Ile Val Gln Leu Val Thr Asn
        50                  55                  60

Gly Lys Asn Ile His Leu His Ala His Ser Leu Val Gly Lys His Cys
65                  70                  75                  80

Glu Asp Gly Ile Cys Thr Val Thr Ala Gly Pro Lys Asp Met Val Val
                85                  90                  95

Gly Phe Ala Asn Leu Gly Ile Leu His Val Thr Lys Lys Lys Val Phe
            100                 105                 110

Glu Thr Leu Glu Ala Arg Met Thr Glu Ala Cys Ile Arg Gly Tyr Asn
        115                 120                 125

Pro Gly Leu Leu Val His Pro Asp Leu Ala Tyr Leu Gln Ala Glu Gly
    130                 135                 140

Gly Gly Asp Arg Gln Leu Gly Asp Arg Glu Lys Glu Leu Ile Arg Gln
145                 150                 155                 160

Ala Ala Leu Gln Gln Thr Lys Glu Met Asp Leu Ser Val Val Arg Leu
                165                 170                 175

Met Phe Thr Ala Phe Leu Pro Asp Ser Thr Gly Ser Phe Thr Arg Arg
            180                 185                 190

Leu Glu Pro Val Val Ser Asp Ala Ile Tyr Asp Ser Lys Ala Pro Asn
        195                 200                 205

Ala Ser Asn Leu Lys Ile Val Arg Met Asp Arg Thr Ala Gly Cys Val
    210                 215                 220

Thr Gly Gly Glu Glu Ile Tyr Leu Leu Cys Asp Lys Val Gln Lys Asp
225                 230                 235                 240

Asp Ile Gln Ile Arg Phe Tyr Glu Glu Glu Asn Gly Gly Val Trp
                245                 250                 255

Glu Gly Phe Gly Asp Phe Ser Pro Thr Asp Val His Arg Gln Phe Ala
            260                 265                 270

Ile Val Phe Lys Thr Pro Lys Tyr Lys Asp Ile Asn Ile Thr Lys Pro
        275                 280                 285

Ala Ser Val Phe Val Gln Leu Arg Arg Lys Ser Asp Leu Glu Thr Ser
    290                 295                 300

```
Glu Pro Lys Pro Phe Leu Tyr Tyr Pro Glu Ile Lys Asp Lys Glu Glu
305                 310                 315                 320

Val Gln Arg Lys Arg Gln Lys
                325
```

<210> SEQ ID NO 3
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Ser Pro Thr Ser Tyr Met Ser Pro Ser Leu Pro Ala Leu Asp Trp Gln
1               5                   10                  15

Leu Pro Ser His Ser Gly Pro Tyr Glu Leu Arg Ile Glu Val Gln Pro
                20                  25                  30

Lys Ser His His Arg Ala His Tyr Glu Thr Glu Gly Ser Arg Gly Ala
            35                  40                  45

Val Lys Ala Ser Ala Gly Gly His Pro Ile Val Gln Leu His Gly Tyr
50                  55                  60

Leu Glu Asn Glu Pro Leu Thr Leu Gln Leu Phe Ile Gly Thr Ala Asp
65                  70                  75                  80

Asp Arg Leu Leu Arg Pro His Ala Phe Tyr Gln Val His Arg Ile Thr
                85                  90                  95

Gly Lys Thr Val Ser Thr Thr Ser His Glu Ile Ile Leu Ser Asn Thr
            100                 105                 110

Lys Val Leu Glu Ile Pro Leu Leu Pro Glu Asn Asn Met Arg Ala Ile
        115                 120                 125

Ile Asp Cys Ala Gly Ile Leu Lys Leu Arg Asn Ser Asp Ile Glu Leu
130                 135                 140

Arg Lys Gly Glu Thr Asp Ile Gly Arg Lys Asn Thr Arg Val Arg Leu
145                 150                 155                 160

Val Phe Arg Val His Ile Pro Gln Pro Asn Gly Arg Thr Leu Ser Leu
                165                 170                 175

Gln Ala Ser Asn Leu Lys Ile Val Arg Met Asp Arg Thr Ala Gly Cys
            180                 185                 190

Val Thr Gly Gly Glu Glu Ile Tyr Leu Leu Cys Asp Lys Val Gln Lys
        195                 200                 205

Asp Asp Ile Gln Ile Arg Phe Tyr Glu Glu Glu Asn Gly Gly Val
210                 215                 220

Trp Glu Gly Phe Gly Asp Phe Ser Pro Thr Asp Val His Arg Gln Phe
225                 230                 235                 240

Ala Ile Val Phe Lys Thr Pro Lys Tyr Lys Asp Ile Asn Ile Thr Lys
                245                 250                 255

Pro Ala Ser Val Phe Val Gln Leu Arg Arg Lys Ser Asp Leu Glu Thr
            260                 265                 270

Ser Glu Pro Lys Pro Phe Leu Tyr Tyr Pro Glu Ile Lys Asp Lys Glu
        275                 280                 285

Glu Val Gln Arg Lys Arg Gln Lys
290                 295
```

<210> SEQ ID NO 4
<211> LENGTH: 487
<212> TYPE: PRT
<213> ORGANISM: Enterobacteria phage T4

<400> SEQUENCE: 4

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415
```

```
Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 5
<211> LENGTH: 676
<212> TYPE: PRT
<213> ORGANISM: Thermus thermophilus
<220> FEATURE:
<223> OTHER INFORMATION: Strain HB8

<400> SEQUENCE: 5

Met Thr Leu Glu Glu Ala Arg Lys Arg Val Asn Glu Leu Arg Asp Leu
1               5                   10                  15

Ile Arg Tyr His Asn Tyr Arg Tyr Val Leu Ala Asp Pro Glu Ile
            20                  25                  30

Ser Asp Ala Glu Tyr Asp Arg Leu Leu Arg Glu Leu Lys Glu Leu Glu
            35                  40                  45

Glu Arg Phe Pro Glu Leu Lys Ser Pro Asp Ser Pro Thr Leu Gln Val
50                  55                  60

Gly Ala Arg Pro Leu Glu Ala Thr Phe Arg Pro Val Arg His Pro Thr
65                  70                  75                  80

Arg Met Tyr Ser Leu Asp Asn Ala Phe Asn Leu Asp Glu Leu Lys Ala
            85                  90                  95

Phe Glu Glu Arg Ile Glu Arg Ala Leu Gly Arg Lys Gly Pro Phe Ala
            100                 105                 110

Tyr Thr Val Glu His Lys Val Asp Gly Leu Ser Val Asn Leu Tyr Tyr
            115                 120                 125

Glu Glu Gly Val Leu Val Tyr Gly Ala Thr Arg Gly Asp Gly Glu Val
            130                 135                 140

Gly Glu Glu Val Thr Gln Asn Leu Leu Thr Ile Pro Thr Ile Pro Arg
145                 150                 155                 160

Arg Leu Lys Gly Val Pro Glu Arg Leu Glu Val Arg Gly Glu Val Tyr
            165                 170                 175

Met Pro Ile Glu Ala Phe Leu Arg Leu Asn Glu Glu Leu Glu Glu Arg
            180                 185                 190

Gly Glu Arg Ile Phe Lys Asn Pro Arg Asn Ala Ala Ala Gly Ser Leu
            195                 200                 205

Arg Gln Lys Asp Pro Arg Ile Thr Ala Lys Arg Gly Leu Arg Ala Thr
            210                 215                 220

Phe Tyr Ala Leu Gly Leu Gly Leu Glu Glu Val Glu Arg Glu Gly Val
225                 230                 235                 240

Ala Thr Gln Phe Ala Leu Leu His Trp Leu Lys Glu Lys Gly Phe Pro
            245                 250                 255

Val Glu His Gly Tyr Ala Arg Ala Val Gly Ala Glu Gly Val Glu Ala
            260                 265                 270
```

```
Val Tyr Gln Asp Trp Leu Lys Lys Arg Arg Ala Leu Pro Phe Glu Ala
            275                 280                 285

Asp Gly Val Val Lys Leu Asp Glu Leu Ala Leu Trp Arg Glu Leu
    290                 295                 300

Gly Tyr Thr Ala Arg Ala Pro Arg Phe Ala Ile Ala Tyr Lys Phe Pro
305                 310                 315                 320

Ala Glu Glu Lys Glu Thr Arg Leu Leu Asp Val Val Phe Gln Val Gly
                325                 330                 335

Arg Thr Gly Arg Val Thr Pro Val Gly Ile Leu Glu Pro Val Phe Leu
                340                 345                 350

Glu Gly Ser Glu Val Ser Arg Val Thr Leu His Asn Glu Ser Tyr Ile
            355                 360                 365

Glu Glu Leu Asp Ile Arg Ile Gly Asp Trp Val Leu Val His Lys Ala
        370                 375                 380

Gly Gly Val Ile Pro Glu Val Leu Arg Val Leu Lys Glu Arg Arg Thr
385                 390                 395                 400

Gly Glu Glu Arg Pro Ile Arg Trp Pro Glu Thr Cys Pro Glu Cys Gly
                405                 410                 415

His Arg Leu Leu Lys Glu Gly Lys Val His Arg Cys Pro Asn Pro Leu
            420                 425                 430

Cys Pro Ala Lys Arg Phe Glu Ala Ile Arg His Phe Ala Ser Arg Lys
        435                 440                 445

Ala Met Asp Ile Gln Gly Leu Gly Glu Lys Leu Ile Glu Arg Leu Leu
        450                 455                 460

Glu Lys Gly Leu Val Lys Asp Val Ala Asp Leu Tyr Arg Leu Arg Lys
465                 470                 475                 480

Glu Asp Leu Val Gly Leu Glu Arg Met Gly Glu Lys Ser Ala Gln Asn
                485                 490                 495

Leu Leu Arg Gln Ile Glu Glu Ser Lys Lys Arg Gly Leu Glu Arg Leu
                500                 505                 510

Leu Tyr Ala Leu Gly Leu Pro Gly Val Gly Glu Val Leu Ala Arg Asn
        515                 520                 525

Leu Ala Ala Arg Phe Gly Asn Met Asp Arg Leu Leu Glu Ala Ser Leu
        530                 535                 540

Glu Glu Leu Leu Glu Val Glu Val Gly Glu Leu Thr Ala Arg Ala
545                 550                 555                 560

Ile Leu Glu Thr Leu Lys Asp Pro Ala Phe Arg Asp Leu Val Arg Arg
                565                 570                 575

Leu Lys Glu Ala Gly Val Glu Met Glu Ala Lys Glu Lys Gly Gly Glu
            580                 585                 590

Ala Leu Lys Gly Leu Thr Phe Val Ile Thr Gly Glu Leu Ser Arg Pro
        595                 600                 605

Arg Glu Glu Val Lys Ala Leu Leu Arg Arg Leu Gly Ala Lys Val Thr
            610                 615                 620

Asp Ser Val Ser Arg Lys Thr Ser Tyr Leu Val Val Gly Glu Asn Pro
625                 630                 635                 640

Gly Ser Lys Leu Glu Lys Ala Arg Ala Leu Gly Val Pro Thr Leu Thr
                645                 650                 655

Glu Glu Glu Leu Tyr Arg Leu Leu Glu Ala Arg Thr Gly Lys Lys Ala
                660                 665                 670

Glu Glu Leu Val
            675
```

-continued

```
<210> SEQ ID NO 6
<211> LENGTH: 559
<212> TYPE: PRT
<213> ORGANISM: Pyrococcus furiosus
<220> FEATURE:
<223> OTHER INFORMATION: Strain ST04

<400> SEQUENCE: 6
```

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Asp
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Asn Glu Ile
65                  70                  75                  80

Glu Asn Ser Val Lys Asp Thr Gly Asp Leu Gly Glu Ser Ile Ala Leu
                85                  90                  95

Ala Val Lys Lys Arg Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Glu Lys Lys Met Lys Tyr Leu Ala Asn Leu Phe Met
    130                 135                 140

Asp Ala Glu Pro Ile Glu Ala Lys Tyr Ile Ala Arg Thr Val Leu Gly
145                 150                 155                 160

Thr Met Arg Thr Gly Val Ala Glu Gly Leu Leu Arg Asp Ala Ile Ala
                165                 170                 175

Leu Ala Phe His Val Lys Val Glu Leu Val Glu Arg Ala Tyr Met Leu
            180                 185                 190

Thr Ser Asp Phe Gly Phe Val Ala Lys Val Ala Lys Leu Glu Gly Asn
        195                 200                 205

Glu Gly Leu Ala Lys Val Gln Val Gln Ile Gly Lys Pro Ile Lys Pro
    210                 215                 220

Met Leu Ala Gln Gln Ala Ala Asn Ile Lys Glu Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Asp Lys Ile Ile Val Tyr Ser Arg Arg Leu Glu
            260                 265                 270

Asn Val Thr Arg Ala Ile Pro Glu Ile Val Glu Ala Leu Lys Gln Ser
        275                 280                 285

Val Lys Pro Asn Lys Ala Ile Val Glu Gly Glu Leu Val Ala Ile Gly
    290                 295                 300

Glu Asp Gly Arg Pro Leu Pro Phe Gln Tyr Val Leu Arg Arg Phe Arg
305                 310                 315                 320

Arg Lys His Asn Ile Gln Glu Met Met Lys Lys Ile Pro Leu Glu Leu
                325                 330                 335

Asn Leu Phe Asp Val Leu Tyr Val Asp Gly Glu Ser Met Ile Asp Val
            340                 345                 350

Lys Phe Ile Asp Arg Arg Lys Lys Leu Glu Glu Ile Ile Glu Pro Asn
        355                 360                 365

-continued

Gly Lys Ile Lys Val Ala Glu Asn Leu Ile Thr Lys Val Glu Glu
    370             375                 380

Ala Glu Ala Phe Tyr Lys Lys Ala Leu Glu Met Gly His Glu Gly Leu
385                 390                 395                 400

Met Ala Lys Arg Leu Asp Ala Thr Tyr Glu Pro Gly Asn Arg Gly Lys
                405                 410                 415

Lys Trp Leu Lys Ile Lys Pro Thr Met Glu Asn Leu Asp Leu Val Ile
                420                 425                 430

Ile Gly Ala Glu Trp Gly Glu Gly Arg Arg Ala His Leu Leu Gly Ser
            435                 440                 445

Phe Ile Leu Gly Ala Tyr Asp Pro Glu Thr Gly Glu Phe Leu Glu Val
450                 455                 460

Gly Lys Val Gly Ser Gly Phe Thr Asp Glu Asp Leu Val Glu Phe Thr
465                 470                 475                 480

Lys Met Leu Lys Pro Leu Ile Ile Lys Glu Gly Lys Arg Val Trp
                485                 490                 495

Ile Glu Pro Lys Ile Val Ile Glu Val Thr Tyr Gln Glu Ile Gln Lys
                500                 505                 510

Ser Pro Lys Tyr Lys Ser Gly Phe Ala Leu Arg Phe Pro Arg Tyr Val
            515                 520                 525

Ala Leu Arg Asp Asp Lys Gly Pro Glu Asp Ala Asp Thr Ile Glu Arg
530                 535                 540

Ile Ala Gln Leu Tyr Glu Leu Gln Glu Arg Met Lys Gly Lys Val
545                 550                 555

<210> SEQ ID NO 7
<211> LENGTH: 536
<212> TYPE: PRT
<213> ORGANISM: Pyrococcus furiosus
<220> FEATURE:
<223> OTHER INFORMATION: Strain ST04

<400> SEQUENCE: 7

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
                20                  25                  30

Val Pro Asp Asp His Leu Glu Phe Ile Pro Tyr Leu Ile Leu Gly Asp
            35                  40                  45

Val Phe Pro Glu Trp Asp Arg Glu Leu Gly Val Gly Glu Lys Leu
        50                  55                  60

Leu Ile Lys Ala Val Ala Met Ala Thr Gly Ile Asp Ala Asn Glu Ile
65                  70                  75                  80

Glu Asn Ser Val Lys Asp Thr Gly Asp Leu Gly Glu Ser Ile Ala Leu
                85                  90                  95

Ala Val Lys Lys Arg Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Glu Lys Lys Met Lys Tyr Leu Ala Asn Leu Phe Met
    130                 135                 140

Asp Ala Glu Pro Ile Glu Ala Lys Tyr Ile Ala Arg Thr Val Leu Gly
145                 150                 155                 160

Thr Met Arg Thr Gly Val Ala Glu Gly Leu Leu Arg Asp Ala Ile Ala
                165                 170                 175

```
Leu Ala Phe His Val Lys Val Glu Leu Val Glu Arg Ala Tyr Met Leu
                180                 185                 190

Thr Ser Asp Phe Gly Phe Val Ala Lys Val Ala Lys Leu Glu Gly Asn
            195                 200                 205

Glu Gly Leu Ala Lys Val Gln Val Gln Ile Gly Lys Pro Ile Lys Pro
        210                 215                 220

Met Leu Ala Gln Gln Ala Ala Asn Ile Lys Glu Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Asp Lys Ile Ile Val Tyr Ser Arg Arg Leu Glu
            260                 265                 270

Asn Val Thr Arg Ala Ile Pro Glu Ile Val Glu Ala Leu Lys Gln Ser
        275                 280                 285

Val Lys Pro Asn Lys Ala Ile Val Glu Gly Glu Leu Val Ala Ile Gly
290                 295                 300

Glu Asp Gly Arg Pro Leu Pro Phe Gln Tyr Val Leu Arg Arg Phe Arg
305                 310                 315                 320

Arg Lys His Asn Ile Gln Glu Met Met Lys Lys Ile Pro Leu Glu Leu
                325                 330                 335

Asn Leu Phe Asp Val Leu Tyr Val Asp Gly Glu Ser Met Ile Asp Val
            340                 345                 350

Lys Phe Ile Asp Arg Arg Lys Lys Leu Glu Glu Ile Ile Glu Pro Asn
        355                 360                 365

Gly Lys Ile Lys Val Ala Glu Asn Leu Ile Thr Lys Lys Val Glu Glu
370                 375                 380

Ala Glu Ala Phe Tyr Lys Ala Leu Glu Met Gly His Glu Gly Leu
385                 390                 395                 400

Met Ala Lys Arg Leu Asp Ala Thr Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Leu Gly Ser
        435                 440                 445

Phe Ile Leu Gly Ala Tyr Asp Pro Glu Thr Gly Glu Phe Leu Glu Val
450                 455                 460

Gly Lys Val Gly Ser Gly Phe Thr Asp Glu Asp Leu Val Glu Phe Thr
465                 470                 475                 480

Lys Met Leu Lys Pro Leu Ile Ile Lys Glu Glu Gly Lys Arg Val Trp
                485                 490                 495

Ile Glu Pro Lys Ile Val Ile Glu Val Thr Tyr Gln Glu Ile Gln Lys
            500                 505                 510

Ser Pro Lys Tyr Lys Ser Gly Phe Ala Leu Arg Phe Pro Arg Tyr Val
        515                 520                 525

Ala Leu Arg Asp Asp Lys Gly Pro
530                 535

<210> SEQ ID NO 8
<211> LENGTH: 1038
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 8

```
Met Gly His His His His His His His His Ser Ser Gly His
1               5                   10                  15

Ile Glu Gly Arg Ala Ser Ala Asp Gly Pro Tyr Leu Gln Ile Leu Glu
            20                  25                  30

Gln Pro Lys Gln Arg Gly Phe Arg Phe Arg Tyr Val Cys Glu Gly Pro
        35                  40                  45

Ser His Gly Gly Leu Pro Gly Ala Ser Ser Glu Lys Asn Lys Lys Ser
    50                  55                  60

Tyr Pro Gln Val Lys Ile Cys Asn Tyr Val Gly Pro Ala Lys Val Ile
65                  70                  75                  80

Val Gln Leu Val Thr Asn Gly Lys Asn Ile His Leu His Ala His Ser
                85                  90                  95

Leu Val Gly Lys His Cys Glu Asp Gly Ile Cys Thr Val Thr Ala Gly
            100                 105                 110

Pro Lys Asp Met Val Val Gly Phe Ala Asn Leu Gly Ile Leu His Val
        115                 120                 125

Thr Lys Lys Lys Val Phe Glu Thr Leu Glu Ala Arg Met Thr Glu Ala
    130                 135                 140

Cys Ile Arg Gly Tyr Asn Pro Gly Leu Leu Val His Pro Asp Leu Ala
145                 150                 155                 160

Tyr Leu Gln Ala Glu Gly Gly Gly Asp Arg Gln Leu Gly Asp Arg Glu
                165                 170                 175

Lys Glu Leu Ile Arg Gln Ala Ala Leu Gln Gln Thr Lys Glu Met Asp
            180                 185                 190

Leu Ser Val Val Arg Leu Met Phe Thr Ala Phe Leu Pro Asp Ser Thr
        195                 200                 205

Gly Ser Phe Thr Arg Arg Leu Glu Pro Val Val Ser Asp Ala Ile Tyr
    210                 215                 220

Asp Ser Lys Ala Pro Asn Ala Ser Asn Leu Lys Ile Val Arg Met Asp
225                 230                 235                 240

Arg Thr Ala Gly Cys Val Thr Gly Gly Glu Glu Ile Tyr Leu Leu Cys
                245                 250                 255

Asp Lys Val Gln Lys Asp Asp Ile Gln Ile Arg Phe Tyr Glu Glu Glu
            260                 265                 270

Glu Asn Gly Gly Val Trp Glu Gly Phe Gly Asp Phe Ser Pro Thr Asp
        275                 280                 285

Val His Arg Gln Phe Ala Ile Val Phe Lys Thr Pro Lys Tyr Lys Asp
    290                 295                 300

Ile Asn Ile Thr Lys Pro Ala Ser Val Phe Val Gln Leu Arg Arg Lys
305                 310                 315                 320

Ser Asp Leu Glu Thr Ser Glu Pro Lys Pro Phe Leu Tyr Tyr Pro Glu
                325                 330                 335

Ile Lys Asp Lys Glu Glu Val Gln Arg Lys Arg Gln Lys Gly Ser Ser
            340                 345                 350

Gly Thr Ser Gly Gly Gly Ser Gly Gly Gly Met Thr Leu Glu Glu Ala
        355                 360                 365

Arg Lys Arg Val Asn Glu Leu Arg Asp Leu Ile Arg Tyr His Asn Tyr
    370                 375                 380

Arg Tyr Tyr Val Leu Ala Asp Pro Glu Ile Ser Asp Ala Glu Tyr Asp
385                 390                 395                 400

Arg Leu Leu Arg Glu Leu Lys Glu Leu Glu Arg Phe Pro Glu Leu
                405                 410                 415
```

```
Lys Ser Pro Asp Ser Pro Thr Leu Gln Val Gly Ala Arg Pro Leu Glu
                420                 425                 430
Ala Thr Phe Arg Pro Val Arg His Pro Thr Arg Met Tyr Ser Leu Asp
            435                 440                 445
Asn Ala Phe Asn Leu Asp Glu Leu Lys Ala Phe Glu Glu Arg Ile Glu
        450                 455                 460
Arg Ala Leu Gly Arg Lys Gly Pro Phe Ala Tyr Thr Val Glu His Lys
465                 470                 475                 480
Val Asp Gly Leu Ser Val Asn Leu Tyr Tyr Glu Glu Gly Val Leu Val
                485                 490                 495
Tyr Gly Ala Thr Arg Gly Asp Gly Glu Val Gly Glu Val Thr Gln
            500                 505                 510
Asn Leu Leu Thr Ile Pro Thr Ile Pro Arg Arg Leu Lys Gly Val Pro
            515                 520                 525
Glu Arg Leu Glu Val Arg Gly Glu Val Tyr Met Pro Ile Glu Ala Phe
            530                 535                 540
Leu Arg Leu Asn Glu Glu Leu Glu Glu Arg Gly Glu Arg Ile Phe Lys
545                 550                 555                 560
Asn Pro Arg Asn Ala Ala Gly Ser Leu Arg Gln Lys Asp Pro Arg
                565                 570                 575
Ile Thr Ala Lys Arg Gly Leu Arg Ala Thr Phe Tyr Ala Leu Gly Leu
            580                 585                 590
Gly Leu Glu Glu Val Glu Arg Glu Gly Val Ala Thr Gln Phe Ala Leu
            595                 600                 605
Leu His Trp Leu Lys Glu Lys Gly Phe Pro Val Glu His Gly Tyr Ala
    610                 615                 620
Arg Ala Val Gly Ala Glu Gly Val Glu Ala Val Tyr Gln Asp Trp Leu
625                 630                 635                 640
Lys Lys Arg Arg Ala Leu Pro Phe Glu Ala Asp Gly Val Val Val Lys
                645                 650                 655
Leu Asp Glu Leu Ala Leu Trp Arg Glu Leu Gly Tyr Thr Ala Arg Ala
                660                 665                 670
Pro Arg Phe Ala Ile Ala Tyr Lys Phe Pro Ala Glu Glu Lys Glu Thr
                675                 680                 685
Arg Leu Leu Asp Val Val Phe Gln Val Gly Arg Thr Gly Arg Val Thr
    690                 695                 700
Pro Val Gly Ile Leu Glu Pro Val Phe Leu Glu Gly Ser Glu Val Ser
705                 710                 715                 720
Arg Val Thr Leu His Asn Glu Ser Tyr Ile Glu Glu Leu Asp Ile Arg
                725                 730                 735
Ile Gly Asp Trp Val Leu Val His Lys Ala Gly Gly Val Ile Pro Glu
                740                 745                 750
Val Leu Arg Val Leu Lys Glu Arg Arg Thr Gly Glu Glu Arg Pro Ile
                755                 760                 765
Arg Trp Pro Glu Thr Cys Pro Glu Cys Gly His Arg Leu Leu Lys Glu
    770                 775                 780
Gly Lys Val His Arg Cys Pro Asn Pro Leu Cys Pro Ala Lys Arg Phe
785                 790                 795                 800
Glu Ala Ile Arg His Phe Ala Ser Arg Lys Ala Met Asp Ile Gln Gly
                805                 810                 815
Leu Gly Glu Lys Leu Ile Glu Arg Leu Leu Glu Lys Gly Leu Val Lys
            820                 825                 830
```

```
Asp Val Ala Asp Leu Tyr Arg Leu Arg Lys Glu Asp Leu Val Gly Leu
            835                 840                 845

Glu Arg Met Gly Glu Lys Ser Ala Gln Asn Leu Leu Arg Gln Ile Glu
850                 855                 860

Glu Ser Lys Lys Arg Gly Leu Glu Arg Leu Leu Tyr Ala Leu Gly Leu
865                 870                 875                 880

Pro Gly Val Gly Glu Val Leu Ala Arg Asn Leu Ala Ala Arg Phe Gly
                885                 890                 895

Asn Met Asp Arg Leu Leu Glu Ala Ser Leu Glu Glu Leu Leu Glu Val
            900                 905                 910

Glu Glu Val Gly Glu Leu Thr Ala Arg Ala Ile Leu Glu Thr Leu Lys
            915                 920                 925

Asp Pro Ala Phe Arg Asp Leu Val Arg Arg Leu Lys Glu Ala Gly Val
    930                 935                 940

Glu Met Glu Ala Lys Glu Lys Gly Gly Glu Ala Leu Lys Gly Leu Thr
945                 950                 955                 960

Phe Val Ile Thr Gly Glu Leu Ser Arg Pro Arg Glu Glu Val Lys Ala
                965                 970                 975

Leu Leu Arg Arg Leu Gly Ala Lys Val Thr Asp Ser Val Ser Arg Lys
            980                 985                 990

Thr Ser Tyr Leu Val Val Gly Glu  Asn Pro Gly Ser Lys  Leu Glu Lys
            995                 1000                1005

Ala Arg  Ala Leu Gly Val Pro  Thr Leu Thr Glu Glu  Glu Leu Tyr
    1010                1015                1020

Arg Leu  Leu Glu Ala Arg Thr  Gly Lys Lys Ala Glu  Glu Leu Val
    1025                1030                1035

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-a

<400> SEQUENCE: 9
aattctcttt aaataaaccc aaggtctcag atttcatgca gattgtgtc              49

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 5Phos-g

<400> SEQUENCE: 10
gacacaatct gcatgaaatc tgagaccttg ggtttattta aagagaatt              49

<210> SEQ ID NO 11
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      10xHis tag

<400> SEQUENCE: 11

His His His His His His His His His His
1               5                   10
```

US 9,719,081 B2

THERMOSTABLE BLUNT-END LIGASE AND METHODS OF USE

SEQUENCE LISTING

The parent application contains a Sequence Listing which was submitted electronically in ASCII format and is hereby incorporated by reference in its entirety. Said ASCII copy, created on May 22, 2014, is named 2028.201_SL.txt and is 35,411 bytes in size.

BACKGROUND

A variety of methods for the amplification of nucleic acids are known. For example, polymerase chain reaction ("PCR") (see, e.g. U.S. Pat. No. 4,683,202) is a popular method for the amplification of nucleic acids. To successfully perform a PCR reaction, the reaction must be performed at multiple different temperatures. This requires hardware or other mechanisms for repeatedly changing the temperature of the PCR reaction. Another method for amplification of nucleic acids is referred to as loop-mediated isothermal amplification ("LAMP") (see, e.g. U.S. Pat. No. 6,410,278). LAMP reactions may be performed isothermally, but typically involve the use of four different primers which recognize a total of six distinct sequences on the target nucleic acid.

Some amplification methods utilize DNA ligation. DNA ligation is a common molecular biology method for joining multiple DNA fragments. Ligases can seal single-strand nicks in duplex DNA, join two pieces with complementary "sticky" ends, and in some cases join two pieces with blunt, non-sticky ends. These methods find use in molecular cloning, nucleic acid diagnostics/detection, nucleic acid amplification, and related activities. Ligases and ligation methods are described, for example, in U.S. Patent Application Publication No. 20120214208; U.S. Pat. No. 7,927,853; de Lumley et al., J. Mol. Biol. (2004) 339, 1059-1075; and Rolland et al., FEMS Microbiol. Lett. (2004) 236, 267-273.

Ligation of two strands of "sticky-ended" DNA is possible, where the substrates to be joined are already pre-positioned in the case of single-strand nick sealing, and the affinity of sticky ends for each other helps drive sticky-end ligation. However, since DNA ligation depends upon the juxtaposition of the two substrates to be joined, DNA ligation is more difficult in situations where the juxtaposition of the two substrates is more difficult, or the strands are likely to become mis-aligned or to separate readily. For this reason, blunt-end and high temperature ligations are two types of ligation that are particularly difficult. Blunt-end ligation, however, depends upon random interactions of the substrates. Two adjustments in blunt-end ligation are commonly made to drive the substrate interactions: low temperature to slow down molecular motion so that random interactions last longer and thus give the ligase a better chance to join the fragments; and molecular crowding reagents such as polyethylene glycol to increase the local concentrations of substrates. Likewise, high temperature ligations are challenging because the interactions of DNA substrates are briefer. The least efficient case is thus a high temperature blunt-end ligation in which molecular crowding reagents cannot be used.

A thermostable ligase, T4 DNA ligase, has been described that can perform blunt-end ligations; however, it is inactivated at temperature above approximately 45° C., so that the range of temperature at which T4 DNA ligase is stable is relatively small. A few other examples of ligases that can be induced to join blunt-ended fragments are known, but these ligases appear to do so only in the presence of high concentrations of molecular crowding agents such as 50% polyethylene glycol (PEG). However, the utility of ligases that require such molecular crowding agents is unclear, since 50% PEG which DNA polymerization (which is required for DNA amplification).

Accordingly, in order to facilitate the generation of amplified nucleic acids for the many and growing number of applications which use amplified nucleic acids, new methods and reagents for the amplification of nucleic acids are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Fusion proteins having thermostable blunt-end ligase activity are provided. Such thermostable blunt-end ligases are useful for DNA amplification, sequencing, production of recombinant DNA (e.g., as a result of such blunt-end fusions) and recombinant fusion proteins (e.g., proteins encoded by recombinant DNA produced as a result of such blunt-end fusions), and for other purposes. Many molecular biology schemes involve ligases; such schemes would benefit from the ability to perform such schemes at elevated temperatures. Thermostable blunt-end DNA ligases disclosed herein are suitable for use in ligation schemes which would benefit from at least one elevated temperature incubation, such as an incubation at about 60-65° C. or higher, including incubation schemes at temperatures as high as about 94° C. A thermostable blunt-end ligase as disclosed herein would be useful for such schemes.

In addition, thermostable blunt-end ligases as disclosed herein may enable high temperature blunt-end ligation without the need for molecular crowding agents. Accordingly, thermostable blunt-end ligase as disclosed herein may be useful for many nucleic acid ligation-amplification schemes, including nucleic acid ligation-amplification schemes which operate at a uniform temperature (e.g., at about 60° C. or higher), and including nucleic acid ligation-amplification schemes which require temperature cycling such as cycling from, e.g., about 94° C. to about 60° C. (or higher) for one, two, three, or more cycles. Nucleic acid ligation-amplification schemes which may benefit from the use of thermostable blunt-end DNA ligases disclosed herein may operate at other temperatures as well, e.g., depending on the temperature resistance characteristics of the novel fusion proteins disclosed herein and the requirements of the difference nucleic acid ligation-amplification schemes. Thermostable blunt-end DNA ligases disclosed herein provide the ability to use high temperatures in nucleic acid ligation-amplification schemes and thereby enable higher specificity target amplification, for example, by permitting temperature denaturation of double-stranded DNA templates as well as specific primer binding.

BRIEF DESCRIPTION OF THE DRAWING

FIG. 1 illustrates the results of a blunt-ended ligation reaction performed at 75° C., and demonstrates that fusion proteins as disclosed herein provide improved blunt-end ligation activity at high temperature.

DETAILED DESCRIPTION

Thermostable, blunt-end ligases are provided herein. As disclosed herein, a thermostable, blunt-end ligase may be prepared by the fusion of a DNA-binding protein to a thermostable ligase. Such ligases produced by these fusions have features and capabilities not provided by their parent compounds alone; the different portions of these fusion proteins provide activities which, when combined, provide new capabilities and unexpectedly improved activity. The DNA-binding protein portion of such fusion proteins is effective to increase the affinity of the ligase to DNA substrates, resulting in enhanced ligation in the challenging conditions of high temperature, blunt-end ligation. The DNA ligase portion surprisingly retains its ability to ligate DNA when combined with a foreign protein (the DNA-binding protein portion). Together, the combined portions unite in novel fusion proteins that are able to ligate blunt-ended DNA substrates even at high temperatures, providing increased ligation activity at high temperatures unavailable by the use of the original, unmodified ligases.

Methods, reagents, devices, systems, and articles of manufacture useful for the practice of the methods, and for the use of reagents, devices, systems, and articles of manufacture disclosed herein, are described, for example, in U.S. Patent Application Ser. No. 61/800,606 and U.S. Patent Application Ser. No. 61/800,925, the entire disclosures of which are hereby incorporated by reference in their entireties.

DEFINITIONS

Before the present novel ligases and ligation methods are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the molecules, compositions, assays, methods, and kits disclosed herein are not limited to the specific embodiments described herein.

It must be noted that, as used in the specification and the appended claims, the singular forms "a," "an" and "the" include plural referents unless the context clearly dictates otherwise. Thus, for example, reference to "a salt" refers to a single salt or mixtures of different salts, and the like.

As used in the description herein and throughout the claims that follow, the meaning of "in" includes "in" and "on" unless the context clearly dictates otherwise.

As used in the description herein and throughout the claims that follow, the meaning of "or" includes both the conjunctive and disjunctive unless the context expressly dictates otherwise. Thus, the term "or" includes "and/or" unless the context expressly dictates otherwise.

In this specification and in the claims that follow, reference will be made to a number of terms, which shall be defined to have the following meanings:

The term "moiety" as used herein refers to any particular composition of matter, e.g., a molecular fragment, an intact molecule, or a mixture of materials.

The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose); as used herein, the following abbreviations for these bases are used to represent nucleic acids in sequence listings identifying and describing their structures (either upper-case or lower-case may be used).

TABLE 1A

| Base (in Nucleic Acid) | Letter Code |
| --- | --- |
| Adenine | A |
| Thymine | T |
| Guanine | G |
| Cytosine | C |
| Uracil | U |

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the "T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' ATAAGC 3', the "T" is upstream from the "G", the "C", and the two "A"s closest to the "G".

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded.

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, a "target" nucleic acid or molecule refers to a nucleic acid of interest. A target nucleic acid/molecule may be of any type, including single-stranded or double stranded DNA or RNA (e.g. mRNA).

As used herein, "complementary" sequences refer to two nucleotide sequences which, when aligned anti-parallel to each other, contain multiple individual nucleotide bases which pair with each other. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

The terms "polypeptide" and "protein" may be used interchangeably to refer to molecules comprised of amino acids linked by peptide bonds. Individual amino acids may be termed "residues" of a polypeptide or protein. The amino acid sequences of polypeptides disclosed herein may be identified by SEQ ID NO: presented as a string of letters, where the letters have the following meanings:

TABLE 1B

| Amino Acid | 3-Letter Code | 1-Letter Code |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A composition may include a buffer. Buffers include, without limitation, phosphate, citrate, ammonium, acetate, carbonate, tris(hydroxymethyl)aminomethane (TRIS), 3-(N-morpholino) propanesulfonic acid (MOPS), 3-morpholino-2-hydroxypropanesulfonic acid (MOPSO), 2-(N-morpholino)ethanesulfonic acid (MES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yl]amino]ethanesulfonic acid (TES), 4-(2-hydroxyethyl)-1-piperazine ethanesulfonic acid (HEPES), acetamidoglycine, tricine (N-(2-Hydroxy-1,1-bis(hydroxymethyl)ethyl)glycine), glycinamide, and bicine (2-(Bis(2-hydroxyethyl)amino)acetic acid) buffers. Buffers include other organic acid buffers in addition to the phosphate, citrate, ammonium, acetate, and carbonate buffers explicitly mentioned herein.

An article of manufacture may comprise a container; and a composition contained within the container, wherein the composition comprises a thermostable ligase. An article of manufacture may comprise a container; and a composition contained within the container, wherein the composition comprises a blunt-end ligase. An article of manufacture may comprise a container; and a composition contained within the container, wherein the composition comprises a thermostable blunt-end ligase. The containers may be formed from a variety of materials such as glass or plastic, and may have a sterile access port (for example the container may be an intravenous solution bag or a vial having a stopper pierceable by a hypodermic injection needle). The article of manufacture may further comprise a label or package insert on or associated with the container indicating that the composition may be used to ligate blunt-ended DNA.

Embodiments of methods and compositions provided herein may be described with reference to FIG. 1.

The novel thermostable blunt-end DNA ligases disclosed herein are comprised of the fusion of a DNA-binding protein with a thermostable ligase. Such fusion proteins as disclosed herein may further comprise other components, such as, for example, peptide linkers, N-terminal or C-terminal additions, tag peptides, and other amino acid sequences, including D-amino acids and peptide mimetics. In addition, fusion protein as disclosed herein may further comprise other components, such as, for example, sugars (e.g., the fusion proteins may be glycosylated), polymers such as polyethylene glycol (e.g., the fusion proteins may be PEGylated), organic moieties other than amino acids, and other additions linked to the fusion proteins. The DNA-binding protein portion increases the affinity of the ligase to DNA substrates, resulting in enhanced ligation in the challenging conditions of high temperature, blunt-end ligation. Many combinations of binding proteins and ligases are possible. For example, the binding protein may be N-terminal or C-terminal relative to the ligase.

It will be understood that multiple combinations of DNA ligases and DBA-binding proteins may be joined to produce the fusion proteins disclosed herein. For example, the following 16 combinations have been constructed:

TABLE 2

| Fusion Proteins Constructed | | |
| --- | --- | --- |
| construct | N-terminal | C-terminal |
| pEE0208 | CTF | T4 |
| pEE0209 | CTF | Tth |
| pEE0210 | CTF | Pfu |
| pEE0211 | CTF | Pfu C23 |
| pEE0212 | T4 | CTF |
| pEE0213 | Tth | CTF |
| pEE0214 | Pfu | CTF |
| pEE0215 | Pfu C23 | CTF |
| pEE0216 | p50 | T4 |
| pEE0217 | p50 | Tth |
| pEE0218 | p50 | Pfu |
| pEE0219 | p50 | Pfu C23 |
| pEE0220 | T4 | p50 |

TABLE 2-continued

Fusion Proteins Constructed

| construct | N-terminal | C-terminal |
|---|---|---|
| pEE0221 | Tth | p50 |
| pEE0222 | Pfu | p50 |
| pEE0223 | Pfu C23 | p50 |

\* Non-underlined text refers to the DNA-binding protein. Descriptions of CTF and p50 are given below.

\* Underlined text refers to the ligase. T4=T4 phage, Tth=*Thermus thermophilus*, Pfu=*Pyrococcus furiosus*, Pfu C23=Pfu with a C-terminal 23-amino acid deletion.

Additional variations are possible, including: (1) different DNA-binding proteins, including thermostable proteins; (2) other DNA ligases, including T4 DNA ligase variants engineered to be thermostable; (3) multiple DNA-binding proteins per ligase, or multiple ligases per DNA-binding protein; (4) transient, non-covalent linkages between the ligase and DNA-binding protein, rather than a protein fusion, to better enable multiple ligation events per ligase molecule; (5) dimers or higher-order multimers of fusion proteins to increase the local concentration of ligase once DNA substrates are bound; (6) different degrees of affinity between the DNA substrate and the DNA-binding protein—for example, using the natural target sequence of p50, GGGAATTCCC (SEQ ID NO: 1), in the DNA target, to enable low picomolar affinity; (7) other nucleic acid modifying enzymes instead of DNA ligase to perform other molecular reactions.

An exemplary method for producing the fusion proteins disclosed herein may be as follows. Fusion proteins may be made by inducing *E. coli* to express DNA constructs made by standard recombinant DNA methods, followed by standard chromatographic protein purification methods. An affinity tag such as polyhistidine may be employed to assist in the protein purification. In the case of thermostable proteins, purification may be assisted by employing heat to denature most *E. coli* host proteins. The purified fusion protein may be used in the same way that a standard, non-heat-stable ligase would be used in the application/reaction of choice, for example in a scheme that depends upon ligation of DNA substrates to make a template for amplification.

The methods disclosed herein can be readily incorporated into and used in device for processing a sample, or a system for processing a sample, which may be an automated assay device, or may be an automated assay system. Such assay devices and assay systems may comprise devices and systems disclosed, for example, in U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244, 946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

Examples

Examples of individual protein components suitable for use in providing fusion proteins as disclosed herein include (the amino acid sequences are provided using the one-letter code for amino acids):

TABLE 3

| Protein Name | Protein Sequence | SEQ ID NO: |
|---|---|---|
| p50 DNA-binding protein (fragment from the human NF-kappa-B protein, accession number NP_003989, amino acids 40-366) | adgpylqileqpkqrgfrfryvcegpshgglpgasseknkksypqvkicnyv gpakvivqlvtngkniḥlhahslvgkhcedgictvtagpkdmvvgfanlgilh vtkkkvfetlearmteacirgynpgllvhpdlaylqaeggggdrqlgdrekelir qaalqqtkemdlsvvrlmftaflpdstgsftrrlepvvsdaiydskapnasnlki vrmdrtagcvtggeeiyllcdkvqkddiqirfyeeeenggvwegfgdfsptd vhrqfaivfldpkykdinitkpasvfvqlrrksdletsepkpflyypeikdkeev qrkrqk | 2 |
| CTF DNA-binding protein (a hybrid from the murine NFATc1 protein, accession number NP_058071, amino acids 390-506; followed by an alanine spacer; followed by a fragment from the human NF-kappa-B protein, accession number NP_003989, amino acids 249-366) | sptsymspslpaldwqlpshsgpyelrievqpkshhrahyetegsrgavkasa gghpivqlhgyleneplṭlqlfigtaddrllrphafyqvhritgktvsttsheiilsn tkvleiplłpennmraiidcagilklrnsdielrkgetdigrkntrvrlyfrvhipq pngrtlslqasnlkivrmdrtagcvtggeeiyllcdkvqkddiqirfyeeeeng gvwegfgdfsptdvhrqfaivfldpkykdinitkpasvfvqlrrksdletsepk pflyypeikdkeevqrkrqk | 3 |
| T4 DNA ligase (accession number NP_049813) | milkilneiasigstkqkqaileknkdnellkrvyrltysrglqyyikkwpkpgi atqsfgmltltdmldfieftlatrkltgnaaieeltgyitdgkkddvevlrrvmmr dlecgasysiankvwpglipeqpqmlassydekginknikfpafaqlkadga rcfaevrgdelddvrllsragneylgldllkeelikmtaearqihpegvlidgelv yheqvkkepegldfflfdaypenskakefaevaesrtasngiankslkgtiseke aqcmkfqvwdyvplveiyslpafrlkydvrfskleqmtsgydkvilienqvv nnldeakviykkyidqglegiilknidglwenarsknlykfkevidvdlkivgi yphrkdptkaggfilesecgkikvnagsglkdkagvksheldrtrimenqny yigkilececngwlksdgrtdyvklflpiairlredktkantfedvfgdfhevtgl | 4 |
| Tth DNA ligase (Thermus Thermophilus strain HB 8, accession YP_144363 .1) | mtleearkrvnelrdliryhnyryyvladpeisdaeydrllrelkeleerfpelks pdsptlqvgarpleatfrpvrhptrmysldnafnldelkafeerieralgrkgpfa ytvehkvdglsvnlyyeegylvygatrgdgevgeevtqnlltiptiprrlkgvp erlevrgevympieaflrineeleergerifknprnaaagslrqkdpritakrglr atfyalglgleeveregvatqfallhwlkekgfpvehgyaravgaegveavyq dwlkkrralpfeadgvvvkldelalwrelgytaraprfaiaykfpaeeketrlld | 5 |

TABLE 3-continued

| Protein Name | Protein Sequence | SEQ ID NO: |
|---|---|---|
| | vvfqvgrtgrvtpvgilepvflegsevsrvtlhnesyieeldirigdwvlvhkag gvipevlrvlkerrtgeerpirwpetcpecghrllkegkvhrcpnplcpakrfea irhfasrkamdiqglgeklierllekglvkdvadlyrlrkedlvglermgeksaq nllrqieeskkrglerllyalglpgvgevlarnlaarfgnmdrlleasleellevee vgeltarailetlkdpafrdlvrrlkeagvemeakekggealkgltfvitgelsrpr eevkallrrlgakvtdsvsrktsylvvgenpgsklekaralgvptlteeelyrllea rtgkkaeelv | |
| Pfu DNA ligase (Pyrococcus furiosus strain ST04, accession YP_006355162) | mrylelaqlyqklekttmkliktrlvadflkkvpddhlefipylilgdvfpewd erelgvgekllikavamatgidaneiensvkdtgdlgesialavkkrkqksffs qpltikrvyqtivkvaettgegsqekkmkylanlfmdaepieakyiartvlgt mrtgvaegllrdaialafhvkvelveraymltsdfgfvakvaklegneglakv qvqigkpikpmlaqqaanikeallemggeaefeikydgarvqvhkdgdkii vysrrlenvtraipeivealkqsvkpnkaivegelvaigedgrplpfqyvlrrfrr khniqemmkkiplelnlfdvlyvdgesmidvkfidrrkkleeiiepngkikv aenlitkkveeaeafykkalemgheglmakrldatyepgnrgkkwlkikpt menldlviigaewgegrrahllgsfilgaydpetgeflevgkvgsgftdedive ftkmlkpliikeegkrywiepkivievtyqeiqkspkyksgfalrfpryvalrd dkgpedadtieriaqlyelqermkgkv | 6 |
| Pfu C23 DNA ligase (C-terminal 23-amino acid deletion of Pfu) | mrylelaqlyqklekttmkliktrlvadflkkvpddhlefipylilgdvfpewd erelgvgekllikavamatgidaneiensvkdtgdlgesialavkkrkqksffs qpltikrvyqtivkvaettgegsqekkmkylanlfmdaepieakyiartvlgt mrtgvaegllrdaialafhvkvelveraymltsdfgfvakvaklegneglakv qvqigkpikpmlaqqaanikeallemggeaefeikydgarvqvhkdgdkii vysrrlenvtraipeivealkqsvkpnkaivegelvaigedgrplpfqyvlrrfrr khniqemmkkiplelnlfdvlyvdgesmidvkfidrrkkleeiiepngkikv aenlitkkveeaeafykkalemgheglmakrldatyepgnrgkkwlkikpt menldlviigaewgegrrahllgsfilgaydpetgeflevgkvgsgftdedive ftkmlkpliikeegkrywiepkivievtyqeiqkspkyksgfalrfpryvalrd dkgp | 7 |

The following provides an example of a fusion protein providing thermostable blunt-end DNA ligase activity: p50-Tth Ligase Fusion, Theranos construct EE0217, e.g. protein prep RDP0078, consists of a His10-containing leader ("His10" disclosed as SEQ ID NO: 11), p50 (shown in italics), a flexible glycine-rich sequence, and the Tth DNA ligase (shown underlined).

(SEQ ID NO: 8)
Mghhhhhhhhhhssghiegrasa*dgpylqileqpkqrgfrfryvcegpsh*

*gglpgasseknkksypqvkicnyvgpakvivqlvtngknihlhahslvgk*

*hcedgictvtagpkdmvvgfanlgilhvtkkkvfetlearmteacirgyn*

*pgllvhpdlaylqaegggdrqlgdrekelirqaaqqtkemdlsvvrlmft*

*aflpdstgsftrrlepvvsdaiydskapnasnlkivrmdrtagcvtggee*

*iyllcdkvqkddiqirfyeeeenggvwegfgdfsptdvhrqfaivfktpk*

*ykdinitkpasvfvlrrksdletsepkpflyypeikdkeevqrkrqkgss*

*gtsgggsgggm*tleearkrvnelrdliryhnyryyvladpeisdaeydrl lrelkeleerfpelkspdsptlqvgarpleatfrpvrhptrmysldnafn ldelkafeerieralgrkgpfaytvehkvdglsvnlyyeeqvlvyqatrq dgevgeevtqnlltiptiprrlkqvperlevrgevympieaflrlneele ergeriknprnaaaqslrqkdpritakrqlratfyalqlqleeverqva tqfallhwlkekgfpvehgyaravqaeqveavyqdwlkkrralpfeadqv vvkldelwrelgytaraprfaiaykfpaeeketrlldvvfqvgrtgrvtp vgilepvflegsevsrvtlhnesyieeldirigdwvlvhkaggvipevlr vlkerrtgeerpirwpetcpecghrllkegkvhrcpnplcpakrfeairh fasrkamdiqglgeklierllekglvkdvadlyrlrkedlvglermgeks aqnllrqieeskkrglerllyalglpqvgevlarnlaarfgnmdrlleas leelleveevgeltarailetkdpafrdlvrrlkeagvemeakekggeal kgltfvitqelsrpreevkallrrlgakvtdsvsrktsylvvgenpgskl ekaralgvptlteeelyrlleartgkkaeelv An example of a blunt-ended ligation reaction performed at 75° C. is provided below. The DNA substrate was a 49-bp duplex DNA made by annealing oligonucleotides EE0139 and EE0140 (sequences below). This blunt-ended duplex was capable of making concatamers upon multiple ligation events. The results of the reaction products were separated by size on an agarose gel, as shown below, demonstrate that: (1) Tth ligase alone (lanes 2-3), although it is known to be capable of sealing DNA nicks at 75° C., performed very little or no blunt ligation in these conditions; (2) T4 DNA ligase with an N-terminal p50 fusion (lanes 4-5) also performed very little blunt ligation in these conditions, although there was some evidence of more ligation than for Tth alone. This observation was believed to be surprising given the temperature sensitivity of T4 ligase alone; (3) Tth DNA ligase with an N-terminal p50 fusion (lanes 6-7) demonstrated a much higher level of blunt-end ligation at 75° C. Thus, the results shown in FIG. 1 below demonstrate that fusion proteins as disclosed herein provide improved blunt-end ligation activity at high temperature.

The invention claimed is:

1. A method of performing a blunt-end DNA ligase reaction, comprising:

Combining DNA molecules to be ligated and a thermostable blunt-end DNA ligase in a solution, wherein said thermostable blunt-end DNA ligase comprises the amino acid sequence: mghhhhhhhhhhssghiegrasadgpylqileqpkqrgfrfryvcegpshgglpgasseknkksypqvkicnyvgpakvivqlvtngknihlhahslvgkhcedgictvtagpkdmvvgfanlgilhvtkkkvfetlearmteacirgynpgllvhpdlaylqaegggdrqlgdrekelirqaalqqtkemdlsvvrlmftaflpdstgsftrrlepvvsdaiydskapnasnlkivrmdrtagcvtggeeiyllcdkvqkddiqirfyeeeenggvwegfgdfsptdvhrqfaivfkpkykdinitkpasvfvqlrrksdletsepkpflyypeikdkeevqrkrqkgssgtsgggsgggmtleearkrvnelrdliryhnyryyvladpeisdaeydrllrelkeleerfpelkspdsptlqvgarpleatfrpvrhptrmysldnafnldelkafeerieralgrkgpfaytvehkvdglsvnlyyeegylvygatrgdgevgeevtqnlltiptiprrlkgvperlevrgevympieaflrineeleergerifknprnaaagslrqkdpritakrglratfyalglgleeveregvatqfallhwlkekgfpvehgyaravgaegveavyqdwlkkrralpfeadgvvvkldelalwrelgytaraprfaiaykfpaeeketrlldvvfqvgrtgrvtpvgilepvflegsevsrvtlhnesyieeldirigdwvlvhkaggvipevlrvlkerrtgeerpirwpetcpecghrllkegkvhrcpnplcpakrfeairhfasrkamdiqglgeklierllekglvkdvadlyrlrkedlvglermgeksaqnllrqieeskkrglerllyalglpgvgevlarnlaarfgnmdrlleasleelleveevgeltarailetlkdpafrdlvrrlkeagvemeakekggealkgltfvitgelsrpreevkallrrlgakvtdsysrktsylvvgenpgsklekaralgvptlteeelyffleartgkkaeelv (SEQ ID NO: 8); and performing a blunt-ended DNA ligation reaction at a temperature of about 60° C. or higher.

2. The method of claim 1, wherein said thermostable blunt-end DNA ligase reaction is performed at a temperature of about 60° C. or higher is performed at a uniform temperature.

3. The method of claim 1, wherein said thermostable blunt-end DNA ligase reaction is performed at a temperature of about 60° C. to about 65° C.

4. The method of claim 1, wherein said thermostable blunt-end DNA ligase reaction is performed at a temperature of about 75° C.

5. The method of claim 1, wherein said thermostable blunt-end DNA ligase reaction comprises temperature cycling.

6. The method of claim 1, wherein said thermostable blunt-end DNA ligase reaction comprises temperature cycling from about 94° C. to about 60° C.

7. The method of claim 1, wherein said thermostable blunt-end DNA ligase reaction comprises two or more cycles of temperature cycling.

8. The method of claim 1, wherein said thermostable blunt-end DNA ligase reaction comprises two or more cycles of temperature cycling from about 94° C. to about 60° C.

9. The method of claim 1, wherein said thermostable blunt-end DNA ligase reaction comprises three or more cycles of temperature cycling.

10. The method of claim 1, wherein said thermostable blunt-end DNA ligase reaction comprises three or more cycles of temperature cycling from about 94° C. to about 60° C.

11. The method of claim 1, wherein said thermostable blunt-end DNA ligase comprises a fusion protein comprising a polymer.

12. The method of claim 1, wherein said thermostable blunt-end DNA ligase comprises a fusion protein comprising a sugar.

13. The method of claim 1, wherein said thermostable blunt-end DNA ligase comprises a fusion protein comprising a sugar and comprising a polymer.

14. The method of claim 1, wherein said thermostable blunt-end DNA ligase comprises a fusion protein comprising a component selected from a peptide linker, an N-terminal addition, a C-terminal addition, and a peptide mimetic.

15. The method of claim 14, wherein said method is performed at about 60° C. to about 65° C.

16. The method of claim 14, wherein said thermostable blunt-end DNA ligase comprises a fusion protein comprising a sugar and comprising a polymer.

17. The method of claim 14, wherein said thermostable blunt-end DNA ligase comprises an affinity tag comprising polyhistidine.

18. The method of claim 1, comprising multiple ligation events effective to provide concatamers.

19. The method of claim 18, wherein said multiple ligation events effective to provide concatamers are performed at about 75° C.

20. The method of claim 18, wherein said thermostable blunt-end DNA ligase comprises a fusion protein comprising a component selected from a peptide linker, an N-terminal addition, a C-terminal addition, and a peptide mimetic.

* * * * *